United States Patent [19]
Sogawa et al.

[11] Patent Number: 4,662,383
[45] Date of Patent: May 5, 1987

[54] ENDOTRACT ANTENNA DEVICE FOR HYPERTHERMIA

[75] Inventors: Akira Sogawa, Tokyo; Kiyoshi Inokuchi, Fukuoka; Keizo Sugimachi, Fukuoka; Hidenobu Kai, Fukuoka; Tetsuya Hotta, Hoya; Yoshio Kawai, Musashino, all of Japan

[73] Assignee: Kureha Kagaku Kogyo Kabushiki Kaisha, Tokyo, Japan

[21] Appl. No.: 535,291

[22] Filed: Sep. 23, 1983

[30] Foreign Application Priority Data

Sep. 27, 1982 [JP] Japan ................. 57-167978

[51] Int. Cl.⁴ ............................................. A61N 5/02
[52] U.S. Cl. .................................. 128/784; 128/401; 128/804
[58] Field of Search ............... 128/804, 784–786, 128/399–401

[56] References Cited

U.S. PATENT DOCUMENTS

| | | | |
|---|---|---|---|
| 3,125,096 | 3/1964 | Antiles et al. | 128/401 |
| 3,837,347 | 9/1974 | Tower | 128/785 |
| 4,140,130 | 2/1979 | Storm, III | 128/804 X |
| 4,375,220 | 3/1983 | Matvias | 128/804 |
| 4,469,103 | 9/1984 | Barrett | 128/400 |

FOREIGN PATENT DOCUMENTS 2407559 8/1975 Fed. Rep. of Germany ...... 128/804
8103616 12/1981 PCT Int'l Appl. ................. 128/804

OTHER PUBLICATIONS

Brezovich et al., "A Practical System . . . Hyperthermia", Int. J. Rad. Oncology Biol. Phys., vol. 17, pp. 423–430, 1981.
Trembly et al., "Practical Embedded Insulated Antenna . . . ", Conf: Proc. 10th Ann. NW. Bio Eng. Conf., Hanover, N.H., Mar. 5–16, 1982, pp. 105–108.
Buck, "Slotted Cylinder Antenna . . . ", Conf: Proc. 8th Eur Microwave Conf, Paris, France, Sep. 4–8, 1978, pp. 548–552.

Primary Examiner—Lee S. Cohen
Attorney, Agent, or Firm—Oblon, Fisher, Spivak, McClelland & Maier

[57] ABSTRACT

An endotract antenna used for hyperthermia treatments. A microwave radiation antenna is surrounded by a balloon-like member made of a thin polymeric film. Tubes for feeding and draining a cooling liquid to and from the inside of the balloon-like member enable the device to effectively warm an endotract lesion such as a tumor by effectively supplying the energy of the microwaves emitted from the antenna to the endotract lesion.

19 Claims, 1 Drawing Figure

ENDOTRACT ANTENNA DEVICE FOR HYPERTHERMIA

BACKGROUND OF THE INVENTION

1. Field of the Invention

This invention concerns an endotract antenna device for hyperthermia and, more specifically, it relates to an endotract antenna device applied to the hyperthermia therapy of tumors or the likes on the organs inside the body.

2. Discussion of the Background

In the hyperthermia therapy for carcinoma, which utilizes the property of the cancer cells that they are less resistant than normal cells against the heat or elevated temperature, a microwave radiation antenna is used to warm the lesion for the therapy.

It is desired that the radiation antenna is as thin as possible so that it may be inserted deeply into the endotract of the body for the therapy of organs inside the body, for example, a digestive organ, and a sort of linear dipole antenna has been employed so far for such a purpose.

However, it is difficult to dispose the conventional linear dipole antenna in direct contact with a surface of the organ at the lesion, and there is fear that gases or the fluid may remain in the gap between the antenna and the surface of the organ.

As a result, the electromagnetic energy emitted from the microwave antenna of such endotract antenna device is absorbed by the body fluid in the gap, or reflected at the gap and can not always serve for effective and uniform warming of the lesion.

SUMMARY OF THE INVENTION

This invention has beenn made in view of the foregoings and it is an ojbect of this invention to provide an endotract antenna device capable of effectively warming the lesion at the wall of the tract or lumen.

The above-mentioned object can be attained according to this invention by an endotract antenna device for hyperthermia comprising an antenna for radiating microwaves, a balloon-like member made of a thin polymeric film and surrounding the antenna, and means for feeding and draining cooling liquid to and from the balloon-like member.

BRIEF DESCRIPTION OF THE DRAWING

This invention is to be described in more details referring to the accompanying drawing, by which the foregoing and other objects, as well as the features of this invention will be made clearer, in which.

DESCRIPTION OF THE PREFERRED EMBODIMENT

Figure 1:
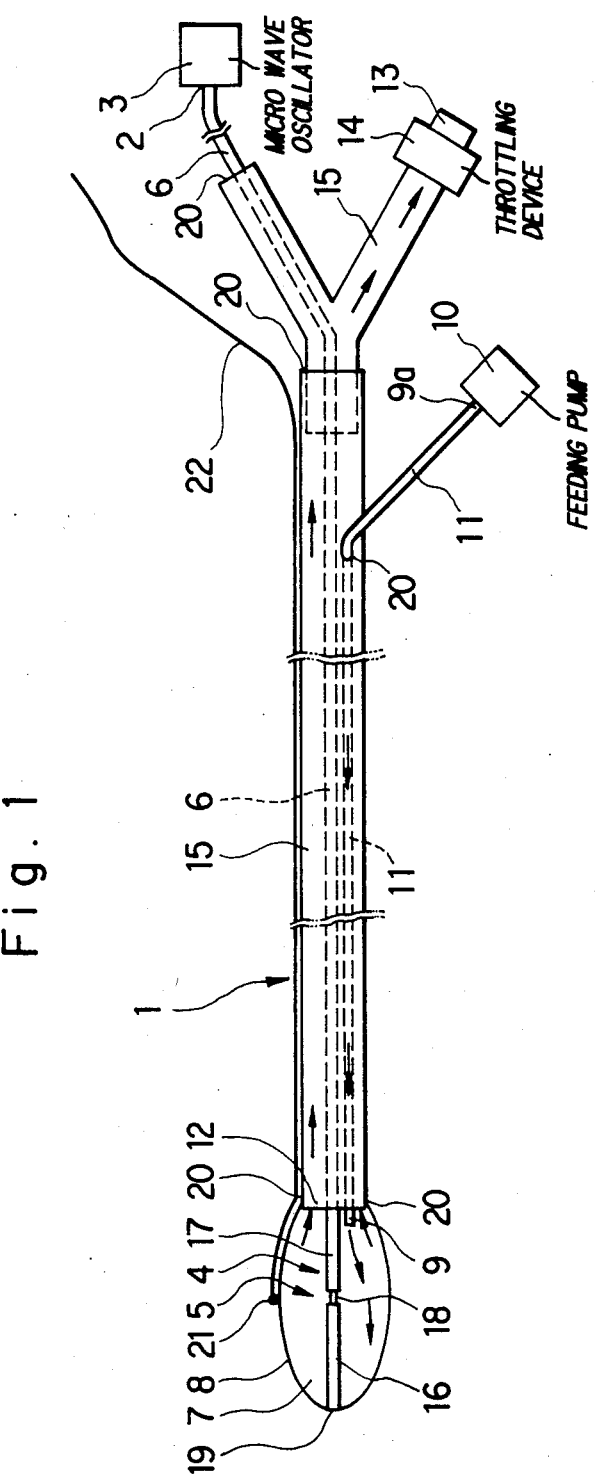
FIG. 1 shows an explanatory view for an endotract antenna device for hyperthermia as a preferred embodiment of this invention, with a balloon being in a slightly expanded state.

Referring to FIG. 1, an endotract antenna device for hyperthermia 1 comprises a coaxial cable 6 for the microwave transmission connected at one end 2 to a microwave oscillator or generator 3 which can continuously generates microwaves, for example, at a frequency of 915 MHz and formed at the other end 4 with a sort of linear dipole antenna 5, a balloon 8 made of a flexible and elastic polymeric thin film and forming a chamber 7 of a variable volume which surrounds the microwave radiation antenna 5 and receives purified water for cooling, a feed tube 11 opened at one end 9 thereof to the water-containing chamber 7 and communicated at the other end 9a thereof with a feed pump 10 so as to feed the purified water into the chamber 7, and a draining tube 15 connected at one end 12 thereof to the balloon 8 and opened at the other end 13 thereof by way of a throttling device 14 for the water pressure control so as to drain the water from the balloon 8. In FIG. 1, the pump 10, the feed tube 11, the throttling device 14 and the draining tube 15 constitute means for feeding and draining the cooling water.

The frequency of the microwaves generated from the oscillator 3 to be applied to tumors at the wall of the tract is usually in the order to between 300–3000 MHz. The frequency of the microwaves may be selected from a plurality of oscillation frequencies that can be generated from the oscillator 3 depending on the size of the antenna 5. The output power of the oscillator 3 may be in the order of 10 to 200 watts for example.

Referring to the coaxial cable 6 which is extended through the draining tube 15 it is preferably designed, for enabling effective transmission of the microwaves and easy insertion of the tube 15 into the tract where the lesion is located, such that the cable has an outer diameter of about 2–10 mm and comprises a central or inner conductor in the form of a single wire or twisted wires made of silver-plated copper wire, an insulator made of a polymeric material with less dielectric loss which is disposed between the central conductor and an outer conductor, the outer shielding conductor in the form of a braided tube or helically wound braided cable made of silver-plated annealed copper wires and the protection coating or jacket at the outer periphery of the outer conductor made of a polymeric material such as fluoro resin, polyvinyl chloride, polyethylene and silicone resin which exhibits no toxicity in the tract.

The microwave radiation antenna 5 comprises a tubular conductor 16 of about $\lambda/4$ in length ($\lambda$ is a wavelength of the microwave in the chamber 7) which is electrically connected to the central conductor and another tubular conductor 17 also of about $\lambda/4$ in length which is electrically connected to the outer conductor and spaced apart from the tubular conductor 16 at a short insulating portion 18.

The tubular conductors 16 and 17 are preferably of an identical shape or configuration. Instead of providing the tubular conductor 16, the top end of the central conductor may be exposed at least by the length of about $\lambda/4$.

The balloon 8 is secured at its base portion to the end 12 of the water-drain tube 15 and secured about at the center of its top end 19 to the top end of the microwave antenna 5. It is preferred that the polymeric film of the balloon 8 is made of highly flexible material so that the film can be in close contact with the surface of the wall of the tract where the lesion is located and that the film is made as thin as possible so that it may absorb less energy of the microwaves emitted or transmitted from the antenna 5, provided that the film has an elasticity sufficient to contain water therein under a certain pressure. In the case of using a thin rubber film for the balloon 8, the film thickness is, for instance, less than 0.5 mm (energy loss of about 30%) and, preferably, less than 0.1 mm (energy loss of about 10–15 %). Although the balloon 8 in the illustrated embodiment is shaped such that it is expandable through an oval or elliptic shape to a generally spheric shape, it may take any other configuration. For instance, the balloon 8 may be protruded longitudinally at the top end 19 and, in this case, the top end of the antenna 5 may be inserted into but not fixed to the elongated recess of the top end 19. The film material for the balloon 8 is preferably rubbery polymeric material, for example, natural rubber or synthetic rubber such as silicone rubber.

In order to transmit the microwaves emitted from the antenna 5 as effectively as possible to the lesion, the cooling medium flowing the inside of the balloon 8, preferably, comprises liquid medium at least mainly composed of water so that the emitted microwaves are transmitted therein substantially at the same wavelength as in the lesion. Purified water with less transmission loss such as absorption is more preferred.

The purified water as the cooling liquid flowing inside of the balloon 8 is kept at an appropriate temperature of about 0°–45° C. and, preferably, about 15°–42° C. so that the temperature at the lesion can be maintained at 42°–45° C. by the purified water in co-operation with the antenna 5.

Further, the flow rate of the cooling water is controlled by the throttling device 14. The throttling device 14 comprises a manually- or automatically-controlled valve, the opening degree of which can be adjusted continuously. The throttling device or valve 14 also serves to produce an adequate pressure within the balloon 8 so as to expand the balloon 8 into an intimate contact with the wall of the tract or lumen organ.

In the illustrated embodiment, the drain tube 15 is constituted as a device main body which is to be inserted through the tract or lumen and through which the coaxial cable 6 and the feed tube 11 are extended. Alternatively, the feed tube 11 may be modified to be constituted as the device main body while extending the drain tube 15 and the coaxial cable 6 inside of the feed tube 11. In this modified embodiment, the base portion of the balloon 8 is secured to the end of the water-feed tube 11. Furthermore, the feed tube 11, the drain tube 15 and the coaxial cable 6 may be bundled in close contact together at their respective outer circumferential surfaces so that the three members form an elongated antenna device main body as a whole, with the balloon 8 being capped over the open ends of the tubes 11, 15 so as to surround the antenna 5, in the case where the assembly can be formed so smooth and thin as can be intaken, for example, from the mouth into the stomach.

The purified water may be used recyclically by connecting the drain tube 15 to the pump 10 by way of a reservoir not shown. Reference numeral 20 in the drawing denotes sealed portions to prevent the leak of the water.

A thermosensor or temperature detector 21 is fixed to the outer surface of the central portion of the circumferential wall of the balloon 8 to detect the temperature at the film or membrane surface of the balloon 8, that is, the temperature at the inner surface of the wall of the tract organ. The thermosensor 21 may be a thermocouple or thermistor. The lead 22 for the thermosensor 21 is disposed along the outer surface of the drain tube 15 constituting the device main body in the illustrated embodiment, it may, however, be passed through the inside of the drain tube 15 as the device main body if desired. The average output from the oscillator 3 and the temperature of the cooling water fed to the balloon 8 are controlled depending on the output signal from the thermosensor 21, that is, on the temperature detected by the sensor 21 so that the temperature of the lesion may be kept at about 42°–45° C. The temperature control may be carried out automatically by a suitable control means.

In the endotract antenna device for hyperthermia 1 constituted as described above, since the microwave radiation antenna 5 is disposed to the inside of the balloon 8 through which the cooling liquid passes, the balloon 8 can be deformed just corresponding to the uneven inner profile of the wall of the tract organ and put to an intimate fitting with the inner surface of the wall, that is, the surface of the lesion by the control of the flow rate and/or the pressure of the cooling liquid flowing inside of the balloon 8, whereby the microwave emitted from the antenna 5 can be transmitted with little transmission loss to the lesion through the purified water in the chamber 7 and the thin film of the balloon 8. Furthermore, control for the temperature and the flow rate of the cooling water flowing inside of the balloon 8 can ensure the hypothermia therapy while preventing or avoiding localized over-heating and maintaining the temperature of the wide lesion area at a temperature of between 42°–45° C.

As described above, according to this invention, since the endotract antenna device for hyperthermia comprises a microwave radiation antennna. a balloon-like member made of a polymeric thin film and surrounding the antenna, and means for feeding and draining a cooling liquid to and from the inside of the balloon-member, the energy of the microwaves emitted from the antenna can be effectively given to the lesion in the tract or lumen organ, thereby enabling to warm the lesion effectively.

What is claimed is:

1. An endotract antenna device for hyperthermia treatment of a tract organ comprising:
   a microwave oscillator;
   a microwave antenna electrically connected to the microwave oscillator for radiating microwaves;
   an expandable balloon-like member made of a flexible and elastic polymeric thin film and defining a variable volume chamber filled with a cooling liquid composed mostly of water and having a low absorption of said microwaves and containing said antenna therein;
   means for feeding and draining said cooling liquid to and from the chamber of said balloon-like member, said feeding and draining means including means for controlling the pressure of the cooling liquid flowing through the chamber of the balloon-like member so as to produce an adequate pressure in the chamber of the balloon-like member and expand the balloon-like member so that the balloon-like member can intimately contact a wall of the tract organ;
   said cooling liquid acting to transmit said microwaves from said antenna to said wall of the tract organ at substantially the same wavelength as in said tract organ to heat said tract organ; and
   means for controlling the temperature of the cooling liquid flowing through the chamber, thereby enabling the temperature and the wall of the tract organ to be controlled.

2. The antenna device as defined in claim 1, in which said antenna comprises a generally linear dipole antenna.

3. The antenna device as defined in claim 2, in which the dipole antenna comprises a pair of conductors each having the same configuration.

4. The antenna device as defined in claim 2, in which the dipole antenna comprises a pair of conductors, one of the paired conductors being a central conductor of a coaxial cable.

5. The antenna device as defined in claim 1, in which said antenna is connected by way of a coaxial cable to the microwave oscillator.

6. The antenna device as defined in claim 1, in which an end of said antenna is fixed to said balloon-like member.

7. The antenna device as defined in claim 1, in which the thin polymeric film is made of rubber.

8. The antenna device as defined in claim 7, in which the rubber is synthetic rubber.

9. The antenna device as defined in claim 7, in which the rubber is natural rubber.

10. The antenna device as defined in claim 1, in which said feeding and draining means further comprises a feeding tube communicating at one end thereof with said balloon-like member so as to feed the cooling liquid into the chamber of said balloon-like member and a draining tube communicating at one end thereof with said balloon-like member so as to drain the cooling liquid from said balloon-like member and connected with the pressure control means.

11. The antenna device as defined in claim 10, in which said feeding and draining means further comprises a pump connected to the other end of the feeding tube so as to supply the cooling liquid by way of the feeding tube to the chamber of said balloon-like member.

12. The antenna device as defined in claim 11, in which said pressure control means comprises a throttling means for controlling the flow rate of the cooling liquid flowing through the chamber of said balloon-like member.

13. The antenna device as defined in claim 12, in which the throttling means is disposed at the other end of the draining tube.

14. The antenna device as defined in claim 13, in which said balloon-like member is capped liquid-tightly over the one end of the draining tube, the feeding tube is inserted in the draining tube at a side of the one end of the draining tube, and a transmission line connecting the microwave oscillator with said antenna is inserted in the draining tube.

15. The antenna device as defined in claim 13, in which said balloon-like member is capped liquid-tightly over the one end of the feeding tube, the draining tube is inserted in the feeding tube at a side of the one end of the feeding tube, and a transmission line connecting the microwave oscillator with said antenna is inserted in the feeding tube.

16. The antenna device as defined in claim 10, in which said cooling liquid temperature control means controls the temperature of the cooling liquid to be supplied by way of the feeding tube to said balloon-like member.

17. The antenna device as defined in claim 1, in which the cooling liquid is water.

18. The antenna device as defined in claim 17, in which the water is purified water.

19. The antenna device as defined in any one of claims 2 to 6, 7 to 18 or 1 in which a thermosensor is disposed on a surface of said balloon-like member.

* * * * *